United States Patent [19]

Junker et al.

[11] Patent Number: 4,578,643
[45] Date of Patent: Mar. 25, 1986

[54] SIMULATION APPARATUS FOR EDDY CURRENT INSPECTION TECHNIQUES

[75] Inventors: Warren R. Junker, Monroeville; Bruce J. Taszarek, Mt. Lebanon; David A. Chizmar, Export, all of Pa.

[73] Assignee: Westinghouse Electric Corp., Pittsburgh, Pa.

[21] Appl. No.: 553,346

[22] Filed: Nov. 18, 1983

[51] Int. Cl.⁴ .................... G01R 35/00; G01N 27/82
[52] U.S. Cl. .................................. 324/202; 324/262; 73/1 R
[58] Field of Search ............... 324/202, 262, 221, 220, 324/226, 225, 237, 238, 240, 219; 73/1 R

[56] References Cited

U.S. PATENT DOCUMENTS

| 3,441,840 | 4/1969 | Randle | 324/202 |
| 3,582,772 | 6/1971 | Hammer | 324/202 |
| 3,609,529 | 9/1971 | Skubiak et al. | 324/202 |

FOREIGN PATENT DOCUMENTS

| 739391 | 6/1980 | U.S.S.R. | 324/202 |
| 866524 | 9/1981 | U.S.S.R. | 324/202 |
| 926585 | 5/1982 | U.S.S.R. | 324/202 |

OTHER PUBLICATIONS

Cowfer et al., "Flaw Simulator for Eddy Current Probe Calibration", *Calibration Devices and Techniques*, NASA Pub. #SP-5907, 1974, p. 21.
Aldeen et al., "Eddy-Current Investigations of Oblique Longitudinal Cracks in Metal Tubes Using a New Mercury Model", *NDT International*, Oct., 1979, pp. 211-216.

*Primary Examiner*—Reinhard J. Eisenzopf
*Assistant Examiner*—Warren S. Edmonds
*Attorney, Agent, or Firm*—L. A. DePaul

[57] ABSTRACT

An apparatus for simulating and analyzing discontinuities in a tube using eddy current inspection techniques is disclosed. The simulation apparatus includes inner and outer tubular members arranged to define an annular chamber having a predetermined tubular configuration corresponding to the tubular configuration of a tube under investigation. The outer tubular member has an opening through the wall thereof and the inner tubular member defines an axially extending hollow interior. A supply of electrically conductive liquid material is provided in the annular chamber, the quantity of liquid material being such as to substantially and completely fill the annular chamber in the vicinity of the opening through the wall of the outer tubular member. A defect simulation member is supported in the opening in the outer tubular member for movement along a predetermined direction extending transverse to the axis of the inner tubular member. Further, an eddy current test probe is positioned in the hollow interior of the inner tubular member adjacent the position of the defect simulation member for generating eddy current responses which are representative of the eddy current responses which would be obtained for a tube having a configuration corresponding to the predetermined tubular configuration and having a discontinuity in the wall thereof corresponding to the predetermined type of discontinuity.

26 Claims, 6 Drawing Figures

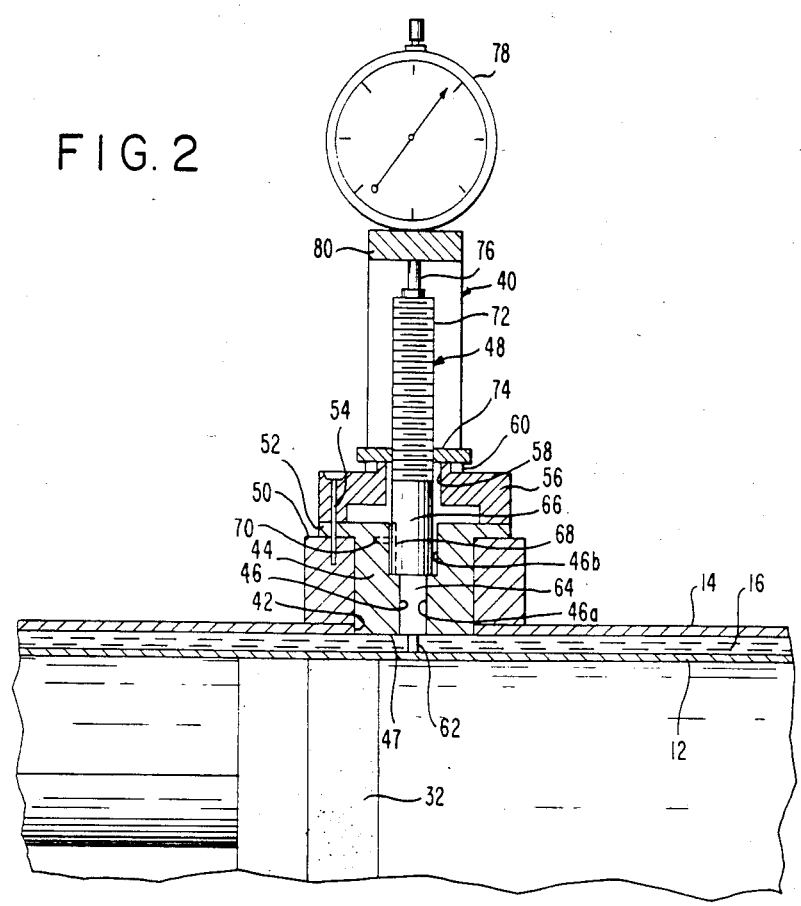
FIG. 2
FIG. 3
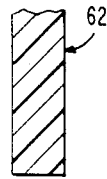
FIG. 4
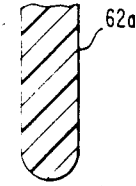
FIG. 5
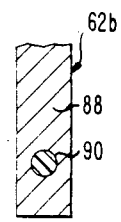
FIG. 6
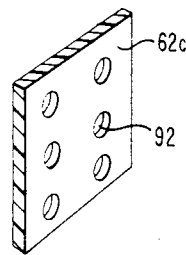

SIMULATION APPARATUS FOR EDDY CURRENT INSPECTION TECHNIQUES

FIELD OF THE INVENTION

The present invention relates to a simulation apparatus for use in connection with eddy current inspection techniques, and more particularly, to an apparatus for simulating and analyzing a wide variety of types of discontinuities or degradation in tubular members. The present invention has particular application in connection with developing and establishing correlations between eddy current inspection responses and the nature and extent of degradation in actual tubular members, and therefore is particularly useful in connection with conducting nondestructive inspection of nuclear steam generator tubing.

BACKGROUND OF THE INVENTION

It is well known that periodic in-service nondestructive inspection of nuclear reactor systems and of components thereof is critical to the reliable operation of such systems. Among the components on which periodic in-service nondestructive inspection must be made is the tubing of nuclear steam generators. Currently, the majority of tubing inspection in nuclear reactor systems is conducted by means of eddy current techniques which measure changes in electromagnetic properties of the tubing caused by tubing degradation, such as for example cracking, thinning, denting, etc.

Nondestructive testing via the use of eddy current techniques relies generally on the principle that when an electrical conductor is placed in an alternating magnetic field, eddy currents are set up in the conductor by electromagnetic induction, the magnitude, phase and distribution of these currents being indicative of the electrical conductivity and physical characteristics of the conductor, e.g., its size, shape, purity or hardness, or by the presence of porosity or discontinuities. These eddy currents, in turn, produce a magnetic field which may be detected and measured as changes in the magnetic field detectable outside of the conductor. More particularly, in eddy current inspection techniques, an alternating or oscillating current excited test coil is placed adjacent to a test piece of unknown characteristics, and the characteristics of the test piece then determined from the effect on the electrical impedance of the test coil.

In connection with nondestructive testing of steam generator tubes of a nuclear reactor system, an eddy current test probe or coil, to which an oscillating current is applied, is placed within a tube. The probe is moved axially along the tube and the effect on the electrical impedance of the test coil, caused by induced eddy currents in the wall of the tubing, is measured to provide an indication of the physical properties and characteristics of the tube. Normally, a plurality of measurements at different oscillating frequencies for the test coil are conducted, it being realized that different frequencies are more sensitive to different conditions. For instance, low frequencies are more sensitive to discontinuities located on the outside of the tube away from the test coil, whereas high frequencies are more sensitive to discontinuities on the inside of the tube, i.e., closer to the test coil. For detected discontinuities, generally only phase angle measurements, representative of the inductive and resistive components of impedance of the test probe, are obtained for each frequency. Such phase angle measurements are believed to be dependent on the radial location of the discontinuity in the tube wall, i.e., the distance between the inner and outer surfaces of the tube; they do not, however, provide an indication of the size or orientation of the discontinuity.

In order to accurately access tube damage as a result of the eddy current responses obtained from such nondestructive testing techniques, it is necessary to develop and establish some type of calibration or correlation between the eddy current responses and the nature and extent of degradation. Presently, no universal mathematical or theoretical correlation exists, and thus the industry relies heavily on emperical correlations developed using laboratory test standards containing simulated degradations. More particularly, laboratory test standards for discontinuity characterization studies are presently generated by providing physical samples or models of the types of tubes under investigation in which various types of discontinuities are physically placed in the wall of the tube, such as by machining. For example, to establish calibration data for a particular discontinuity, it is necessary to make a number of models in which the particular discontinuity extends to different depths in the wall of the tube. Eddy current inspection tests are then conducted at different frequencies on the different physical models to obtain a set of curves showing the variation in eddy current responses for the different depths and different frequencies. The eddy current response obtained with respect to actual steam generator tubes is then compared to the obtained calibration data to make an assessment of the tubing damage which exists in the actual steam generator tubes.

As can be appreciated, preparation of adequate test models is an expensive and tedious operation as it is necessary to precisely machine the particular types of defects at precise locations or positions in the test models. Furthermore, it is not always possible to fabricate physical test specimens which simulate the potential types of tubing damage or degradation which is encountered from in-service operation for steam generator tubings in a nuclear environment.

Consequently, a significant need exists for a simulation apparatus which is capable of accurately simulating all types of degradation which might be expected to be encountered in tubes, and further, one which is capable of varying the position and orientation of the simulated discontinuities in a simple, noncomplex and accurate manner without having to physically construct a number of different test models. Also, it is desirable that the simulation apparatus be able to generate or establish calibration data in a rapid manner with a minimum amount of effort.

In this regard, it has previously been suggested in connection with developing an improved understanding of eddy current inspection concepts to use mercury models containing simulated degradation. For example, in an article entitled, "Eddy-Current Investigations of Oblique Longitudinal Cracks in Metal Tubes Using a Mercury Model" by Aldeen and Blitz, appearing in the October 1979 issue of *N.T.D. International*, at pages 211-216, there is disclosed a mercury model for eddy current tube testing analysis and investigation. The particular model disclosed in this article comprises inner and outer concentrically arranged glass tubes in which the ends of the glass tubes are mounted in a pair of reservoirs which contain mercury for filling the annular space between the glass tubes. A simulated defect is provided for placement in the annular space of mercury along the entire length of the tube. More particularly, in the disclosed arrangement, a long plastic strip, designed to simulate a longitudinal crack of a uniform width and thickness, is held at its ends by a pair of spindles located in the mercury reservoirs. Through the use of a relatively complex mechanism comprising cog wheels and beveled gears mounted on sliding forks, the depth and orientation of the long plastic strip within the annular space can be adjusted. In order to conduct eddy current measurements with respect to the mercury model, different test coils designed for use in connection with different frequency ranges are provided, each of the test coils being adapted to be arranged between the ends of the glass tubes and encircling the outer tube.

While the apparatus disclosed in the above-noted article does provide a model for generating eddy current response in tubes, it is subject to a number of constraints or limitations in connection with providing a suitable simulation apparatus for generating eddy current calibration data for a wide variety of types of defects in tubes in a simple and efficient manner. For instance, in order to conduct discontinuity simulation experiments with respect to other types of defects, it is necessary to disassemble the apparatus to remove the simulated defect and replace it with a different type of simulated defect. Furthermore, in order to conduct tests using different frequencies in which a different test coil is utilized, it is again necessary to disassemble the apparatus, remove the one test coil and replace it with a different test coil. Still further, the above-noted prior art apparatus is only suitable for conducting eddy current measurements with respect to defects which extend along the entire longitudinal length of the mercury tube. Thus, for example, it is not possible to conduct eddy current tests with respect to defects which are designed to simulate holes which extend over only a short longitudinal distance or to simulate holes or cracks which extend completely through the side wall of a tube. Even if a hole-type simulated defect were provided in the above-noted apparatus, a discontinuity would still exist along the entire longitudinal length of the tube by virtue of the disclosed support arrangement in which the simulated defect is held at the opposite ends of the tube. Thus, while the disclosed apparatus is useful for conducting eddy current measurements with respect to certain types of defects, its versatility is greatly limited, particularly in terms of its ability to simulate a wide variety of types of degradations or defects.

SUMMARY OF THE INVENTION

In accordance with the present invention, there is provided a simulation apparatus which overcomes the above-noted and other disadvantages of the prior art. More particularly, the simulation apparatus of the present invention is capable of accurately simulating virtually any type of degradation which might be encountered in tubes. Further, the simulation apparatus is operative to adjust the orientation and position of the simulated discontinuity in a simple, noncomplex manner so as to provide the capability of generating accurate calibration or correlation data between the eddy current responses obtained and discontinuities or degradation in actual tubes.

The simulation apparatus in accordance with the present invention comprises an inner tubular member and an outer tubular member arranged to define an annular chamber having a predetermined tubular configuration, the outer tubular member having an opening through the side wall thereof and the inner tubular member defining an axially extending hollow interior extending along the axis of the inner tubular member. A supply of electrically conductive liquid material is provided in the annular chamber, the quantity of liquid material being such as to substantially completely fill the annular chamber in the vicinity of the opening in the wall of the outer tubular member. A defect simulation member is supported in the opening of the outer tubular member for movement along a predetermined direction extending transverse to the axis of the annular tubular member. The defect simulator member includes a simulator portion which is adapted to be placed in the electrically conductive liquid material in the annular chamber. The simulator portion is made at least partially of a material which has an electrical conductivity different from that of the liquid material filling the annular chamber, and has a predetermined configuration corresponding to a predetermined type of discontinuity in a tube. Means are provided for adjusting the position of the simulator portion within the annular tube along the predetermined direction. In addition, an eddy current test probe is positioned in the hollow interior of the inner tubular member adjacent the position of the defect simulation member for generating eddy current responses which are representative of the eddy current responses which would be obtained for a tube having a configuration corresponding to the predetermined tubular configuration and having a discontinuity in the wall thereof corresponding to the predetermined type of discontinuity.

With the simulation apparatus in accordance with the present invention, changes in the type of simulated discontinuity and adjustment of their orientation and position can be readily accomplished without having to disassemble the concentrically arranged tubular members having the liquid material therebetween. In addition, it is possible to change eddy current test probes without having to disassemble the apparatus, since the test probes may simply be inserted and removed from the inner tubular member through the end thereof without interference from the closure of the ends of the annular chamber defined between the inner and outer tubular members. Accordingly, it will be appreciated that the simulation apparatus in accordance with the present invention provides for a great degree of flexibility in terms of the types of discontinuities which may be investigated as well as in terms of the positioning and orientation of such discontinuities within the annular chamber, thereby affording the capability of simulating discontinuities in the wall of the tube of the particular configuration corresponding to the predetermined tubular configuration of the annular chamber. Furthermore, investigation can be easily made at different frequencies utilizing different eddy current test probes. Thus, with the present invention, it is possible to establish in a relatively simple and efficient manner correlations between eddy current inspection responses and the nature and extent of degradation of actual tubing. In addition to expediting the preparation of calibration data, with the present invention an improved understanding of eddy current inspection concepts can be obtained.

In accordance with a preferred embodiment of the present invention, indicator means are provided for indicating the portion of the simulator portion in the electrically conductive liquid material in the annular chamber. Also, in accordance with a preferred embodiment, a removable insert member is mounted in the opening through the outer tubular member, the insert member including a surface conforming to the inner surface of the outer tubular member when it is supported in the opening. The insert member also preferably includes a bore therethrough extending in the predetermined direction of movement of the defect simulator member and having a cross-sectional configuration corresponding to the cross section of a portion of said defect simulator member so that the defect simulator member will be slidably supported in the insert for movement along the axis of said bore. Further, the insert member preferably includes a stop thereon and the adjustment comprises a threaded wheel member mounted to a threaded portion of the defect simulator member and engageable with the stop to support the simulator portion at a desired position in the annular chamber. In this manner, rotation of the threaded member serves to move the defect simulator member along the axis of the bore to adjust the position of the simulator portion within the annular chamber.

Further, in accordance with a preferred embodiment, the defect simulator member is made at least partially of a nonelectrically conductive material, such as plastic to simulate a void space in a tube wall. For instance, the simulator portion could be formed in the shape of a small cylinder to simulate a hole or a plate to simulate a crack.

These and further features and characteristics of the present invention will be apparent from the following detailed description in which reference is made to the enclosed drawings which illustrate preferred embodiments of the present invention.

BRIEF DESCRIPTION OF THE DRAWINGS

FIG. 2 is a cross-sectional side elevational view of the apparatus shown in FIG. 1, illustrating how the defect simulator member thereof is supported and the position of the simulator portion adjusted within the annular chamber.

FIGS. 3-5 are side elevational views of different simulator portions of the defect simulator member which may be utilized in the simulation apparatus of the present invention to simulate different types of discontinuities in a tube.

FIG. 6 is a perspective view of a further alternative simulator portion of a defect simulator member which may be utilized in the simulation apparatus of the present invention.

DESCRIPTION OF THE PREFERRED EMBODIMENTS

Figure 1:
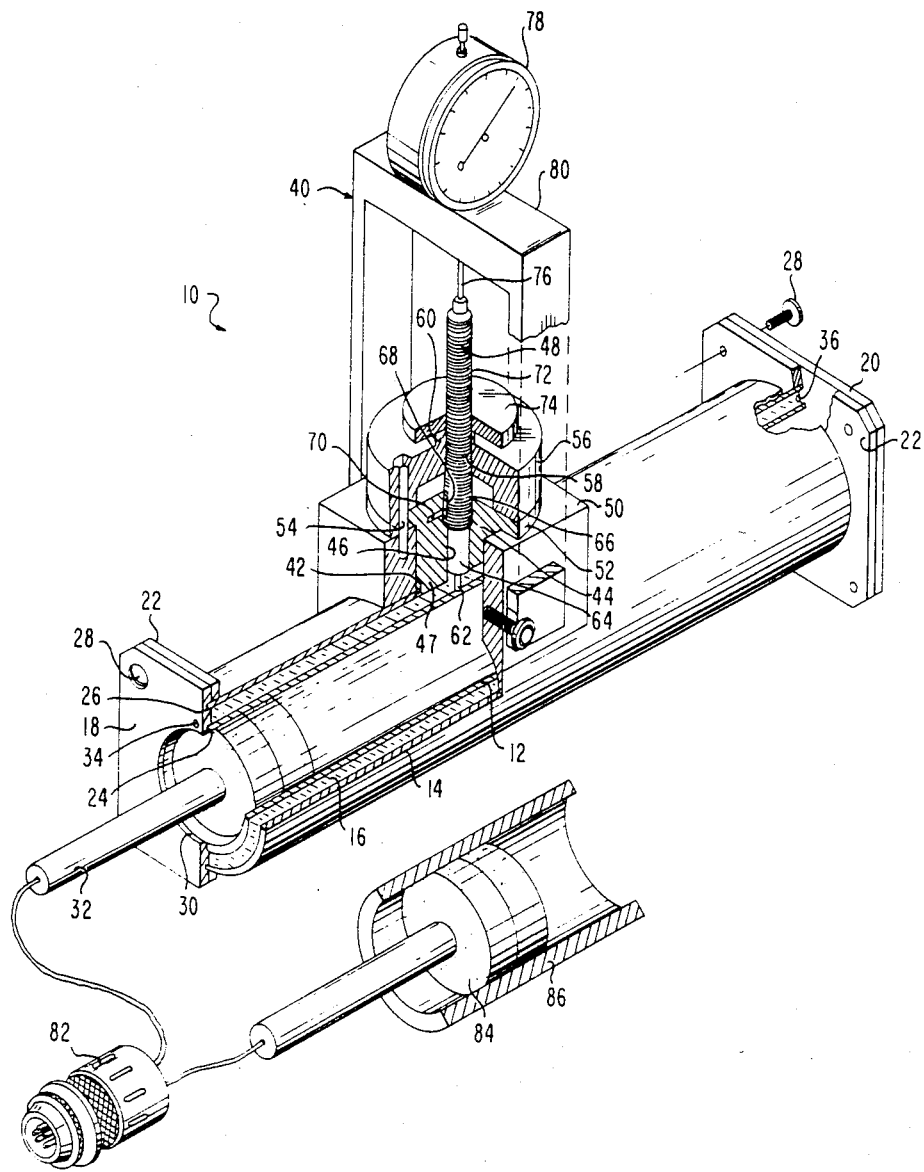
FIG. 1 is a perspective view of the simulation apparatus in accordance with the present invention, portions thereof being cut away to illustrate the construction and arrangement of the various components thereof.

Referring now to the drawings wherein like reference characters represent like elements, there is illustrated in FIG. 1 a perspective view, partially cut away, of the simulation apparatus 10 in accordance with the present invention for use in simulating and analyzing discontinuities in tubes using eddy current inspection techniques. More particularly, the simulator apparatus 10 in accordance with the present invention is particularly well suited for use in connection with developing eddy current calibration data for a wide variety of different types of discontinuities located at varying depths in the wall of tubes, and thereby establishing correlations between eddy current responses and the nature and extent of degradation in actual tubing. As the simulator apparatus 10 in accordance with the present invention is particularly useful in connection with providing calibration data for use in connection with in-service nondestructive inspection of nuclear steam generator tubing, it will be described with reference thereto. However, it should be appreciated that the simulation apparatus 10 may be used in connection with generating eddy current calibration responses or data for use in connection with the determination of the characteristics and properties of tubular members in general.

Further in this regard, and as noted hereinabove, calibration data for eddy current inspection techniques with respect to tubes has previously been generated using physical models of tubes in which particular types of discontinuities have been machined or placed in the wall of the test model. The particular eddy current inspection equipment and techniques used with the present invention may be the same type of inspection equipment and techniques used in the past for generating eddy current responses with respect to such prior art physical samples or test models and also used in connection with performing inspections on actual tubes. Such eddy current inspection equipment and techniques form no part of the present invention and therefore will not be described in detail herein.

Briefly, however, in accordance with such prior eddy current inspection techniques, an eddy test probe, which comprises an electrical coil, is placed interiorly in a tube or test sample and moved axially therealong. An oscillating or alternating current is applied by the test equipment to the test probe and readings are obtained which detect and measure the changes in impedance of the test coil as the test coil is moved along the tube. The changes in impedance represent changes in the conductivity of the test piece which is related to the absolute electrical conductivity, or some property related thereto, of the tubing. For instance, the responses may comprise phase angle measurements which are representative of the inductive and resistive components of the changes in impedance, the responses being displayed on a suitable display device such as an oscilloscope. Still further, in order to increase the sensitivity of the obtained readings to small changes in impedance, difference type measurements are generated in which a reference measurement, obtained for example by means of a second coil with respect to a reference tube having no defects therein, is substracted from the measurements on the tube having the defect therein. In some instances, the second coil is provided in axially spaced relationship from the first coil on the test probe so as to obtain measurements on a different section of the tubular member under investigation. One typical eddy current inspection apparatus which is capable of generating the above-noted types of eddy current responses, and which may be used in connection with apparatus of the present invention, is a Zetec MIZ 12 Multiple Frequency Eddy Current Test Instrument.

As best seen in FIG. 1, the basic simulation apparatus 10 in accordance with the present invention includes a pair of tubular members 12, 14 of differing diameters arranged in a concentric fashion to define an annular chamber 16 therebetween. Each of the tubular members is constructed of a nonelectrically conductive material such as plastic or glass. The inner and outer tubular members 12, 14 are supported in concentric arrangement by means of suitable end support members 18, 20. More particularly, adjacent to each end of the outer tubular member 14 there is provided a fixed support plate 22 fixedly attached to the outer surface thereof in a suitable manner, such as by means of a suitable adhesive. In order to support the inner tubular member 12 in concentric relationship thereto, a pair of removable end plates 18, 20 are provided, each having a pair of concentric grooves 24, 26 machined in one surface thereof. The diameters of the grooves 24, 26 correspond to the diameters of the inner and outer tubes 12, 14 respectively and the width of the grooves 24, 26 correspond to the wall thickness of the inner and outer tubular members 12, 14. The ends of the inner tubular member 12 are received in the inner annular grooves 24 of the end plates 18, 20, while the ends of the outer tubular member 14 which extend beyond the fixed support plates 22 are received within the outer annular grooves 26 of the end plates 18, 20, and the end plates 18, 20 then secured to the fixed support plates 22 attached to the outer tube 14, such as with screws 28. In this manner, the inner tube 12 is concentrically positioned with respect to the outer tube 14, and further, the ends of the annular chamber 16 defined between the inner and outer tubes 12, 14 are sealed against leakage. While a simple force fit onto the ends of the tubular members 12, 14 and securement of the end plates 18, 20 to the support plates 22 is normally sufficient to seal the annular chamber 16, if necessary suitable means such as O-rings or gasket material could be provided about or in the grooves 24, 26 to insure a leakproof closure. Further, it will be noted from FIG. 1 that each of the removable end plates 18, 20 has an opening 30 therethrough adjacent the inner groove 24 thereof so that an eddy current test coil or probe 32 may be inserted therethrough into the hollow interior defined by the inner tubular member 12, as more fully described hereinbelow.

The annular chamber 16 between the inner and outer tubular members 12, 14 is filled substantially completely with an electrically conductive liquid material, and preferably an electrically conductive nonmagnetic material, such as mercury, to thereby define an electrically conductive, tubular shaped test model on which eddy current inspection may be performed. The configuration of the annular chamber 16 substantially corresponds to the tubular configuration of the tube under investigation, e.g., a steam generator tube. In other words, the inner and outer diameters of the chamber 16 (i.e., corresponding to the outer diameter of the inner tubular member 12 and the inner diameter of the outer tubular member 14 respectively) correspond to the inner and outer diameters of the tube under investigation. In this regard, it will be noted that since the inner and outer tubular members are made of a nonelectrically conductive material, only the liquid filled annular chamber 16 will be electrically conductive.

In order to fill the annular chamber 16 with mercury or another electrically conductive liquid, a suitable fill opening 34 is provided in one of the end plates 18 in alignment with the end of the annular chamber 16, i.e., between the pair of annular grooves 24, 26. A vent opening 36 is also provided in alignment with the end of the annular chamber 16 for venting of air from the annular chamber 16 during the filling process. In this regard, it is important to vent substantially all of the air from the chamber 16 so that the mercury will substantially completely fill the annular chamber 16. Further, it is preferable that the concentrically supported inner and outer tubular members 12, 14 be oriented at an angle, during the filling operation, and even during generation of test data, so that any air which might be in the chamber will be collected at one end of the concentric tubes 12, 14. For example, the concentrically arranged tubular members 12, 14 may be inclined at an angle of 30° with respect to the horizontal. Here it should be noted that the presence of any air in the vicinity of simulated defect could adversely affect the validity of the measurements and calibration data obtained.

In accordance with the present invention, a defect simulator and adjustment unit 40 is mounted to the outer tubular member 14 and is adapted to position a simulated discontinuity into the formed tube of mercury at a desired radial location, i.e., at a desired location in the wall of the mercury tube. More particularly, the outer tubular member 14 includes an opening or window 42 cut through the wall thereof intermediate the ends of the outer tube 14. A removable insert support member 44 is positioned in tight fitting relationship in the window 42, and includes a bore 46 (as best seen in FIG. 2) extending therethrough for receipt of a defect simulator member 48 for movement along the axis of the bore 46 into and out of the chamber 16 provided between the inner and outer tubular members 12, 14. In this regard, the insert member 44 includes an inner or lower surface 47 which has been machined to match the inner surface of the outer tube 14 so that the outer tube 14, with the insert member 44 mounted therein will be smooth and cylindrical so as to provide an essentially cylindrical outer surface for the defined tube of mercury. In this regard, it is important to machine the inner surface 47 of the insert member 44 to precisely match the inner surface of the outer tubular member 14 and polish same so that no air bubbles will be provided in the vicinity of the insert member 44 between the mercury and the inner surface 47 of the insert member 44.

Further, a heavy support block 50, having a bore therein corresponding to the shape of the insert member 44, is attached to the outer tubular member 14 in alignment with the window 42 for supporting the removable insert member 44 therein. The opening or window 42 cut in the outer tubular member 14 and the bore through the heavy support block 50 are machined to provide substantially a tight fitting relationship when the insert member 44 is inserted therein. In the preferred embodiment, a suitable sealing lubricant, such as grease or petroleum jelly, is provided to insure against any leakage of mercury from annular chamber 16 between the window 42 and the insert member 44.

In order to aid in proper positioning of the insert member 44 within the support block 50 and the outer tubular member 14, and also to aid in removing the insert member 44 from the support block 50, an enlarged lip section 52 is provided on the insert member 44 which is adapted to be supported on the upper surface of the support block 50. Preferably, the lip section 52 is constructed such that the inner surface 47 of the insert member 44 is precisely matched with the inner surface of the outer tubular member 14 when the lip section 52 rests on the upper surface of the support block 50. Minor adjustment of the position of the insert member 44 can be accomplished by means of threaded adjustment members 54 received in threaded apertures provided in the insert member 44 and support block 50. An adjustment stop block 56 having an aperture 58 therethrough is mounted to the lip section 52 of the insert member 44 with the aperture 58 thereof aligned with the bore 46 in the insert member 44. The upper surface of the adjustment stop block 56 includes a raised stop collar 60 thereon for a purpose to be described more fully hereinbelow.

As noted above, the insert member 44 includes a bore or opening 46 therethrough for receipt of the defect simulator member 48 for movement along the axis thereof into the chamber 16 provided between the inner and outer tubes 12, 14, i.e., into the "wall" of the tubular configuration of mercury. In this regard, the defect simulator member 48 is mounted for movement along the bore 46 of the insert member 44 in a manner such that the position of the end of the defect simulator member 48 can be precisely controlled.

More particularly, as best seen in FIG. 2, the defect simulator member 48 in accordance with the present invention comprises an elongated member having a plurality of different sections therealong. The lowermost section 62 comprises a simulator portion or section which is shaped and configured to correspond to the particular type of discontinuity under investigation. For instance, the simulator portion 62 may comprise a small cylinder to correspond and simulate to a flat bottom hole, such as shown in FIG. 3. Above the simulator section or portion 62, there is provided a generally cylindrical seal section 64 which is adapted to fit within a lower cylindrical section 46a of the bore 46, the cylindrical section 46a corresponding in size to seal section 64 of the defect simulator member 48. Upon assembly, the cylindrical seal section 64 of the defect simulator member 48 may be provided with a coating of suitable sealing lubricant, such as grease or petroleum jelly, in order to permit axial sliding movement of the defect simulator member 48 within the insert member 44 while still sealing the exterior of the insert member 44 from any leakage of mercury. Above the cylindrical seal section 64, there is provided another cylindrical section 66 having a longitudinally extending groove 68 therein for receipt of an anti-rotation pin 70 mounted in an enlarged section 46b of the bore 46 of the insert member 44. The anti-rotation pin 70 serves to prevent rotation of a defect simulator member 48 within the insert member 44 while still permitting axial sliding movement thereof for adjustment of the position or depth of the simulator portion 62 within the wall of the tube of mercury.

A threaded section 72 of the defect simulation member 48 is provided above the anti-rotation section 66. This threaded section 72 is provided with a threaded knurled wheel 74 thereon for rotation relative to the defect simulator member 48 for adjusting and precisely controlling the axial position of the defect simulator member 48. In this regard, the knurled wheel 74 is adapted to rest against the stop collar 60 to support the defect simulator member 48, rotation of the knurled wheel 74 serving to raise and lower the defect simulator member 48 relative to the fixed support block and insert member, and thus relative to the formed tube of mercury. It should be noted in this regard that the aperture 58 through the adjustment stop block 56 is larger than the outer diameter of the defect simulator member 48 so that there is no interference of movement of the defect simulator member 48 presented thereby. Finally, the uppermost section 76 of the defect simulator member 48 extends above the threaded section 72 and is connected to a suitable indicator device 78, such as a dial gauge. As best seen in FIG. 1, the dial gauge 78 in turn is supported by U-shaped brackets 80 secured to the support block 50 affixed to the outer tubular member 14. It will be appreciated that by virtue of the connection of the end section 76 of the defect simulator member 48 to the dial gauge 78, raising and lowering of the defect simulator member 48 by rotation of the knurled wheel 74 will be indicated on the dial gauge 78.

The use of the simulation apparatus 10 of the present invention in connection with simulating and analyzing defects in tubes will now be described.

Initially, the inner and outer tubular members 12, 14 are assembled together to form the annular chamber 16, and the entire chamber 16 then filled with a supply of liquid mercury through the fill opening 34 in one of the end plates 18. During the filling operation, air in the chamber 16 will be evacuated through the vent opening 36. As noted above, it is preferable that the assembled tubes 12, 14 be inclined so that any air trapped in the chamber 14 is collected at the raised end. Next, with the insert member 44 properly positioned in the support block 50, the knurled wheel 74 on the defect simulator member 48 is rotated to raise the wheel 74 off the stop collar 60 and allow the simulator portion 62 to be lowered until the end thereof engages the outer surface of the inner tubular member 12 (see FIG. 2). The dial gauge 78 is then adjusted to show a zero setting, thereby indicating that the end of the defect simulator member 48 extends completely through the wall of the mercury tube. The knurled wheel 74 may then be rotated downwardly until it is in contact with the raised stop collar 60. Further rotation of the knurled wheel 74 will serve to raise the defect simulator member 48 along the axis of the bore 46 in the insert member 44 so that the end thereof is raised or moved away from the inner tube 12. It will be noted that during the movement of the defect simulator member 48, the rotational or angular orientation thereof will not change since the anti-rotation pin 70 prevents rotation in the defect simulation member 48; rather the defect simulator member 48 will simply move along the bore 46 through the insert member 44. The dial gauge 78, coupled to the upper section 26 of the defect simulator member 48, will indicate the distance between the end of the simulator portion 62 and the outer surface of the inner tube 12 (i.e., the inner surface of the mercury tube).

Once the defect simulator member 48 is in the desired position, an eddy current test probe 32 is inserted into the hollow interior of the inner tubular member 12 through the opening 30 in the end plate 18 and moved past the location of the defect simulator member 48. The eddy current test probe 32, which comprises an electrical coil, is connected through a suitable connection device 82 to a conventional eddy current inspection instrument (not shown) which serves to apply an oscillating current to the coil 32 and to detect and measure changes in impedance of the test probe or coil 32 as it is moved axially along the inner tubular member 12. The test probe 32 is preferably sized to provide a relatively tight fit with the inner tubular member 12, i.e., the outer diameter of the test probe 32 is only slightly less than the inner diameter of the inner tubular member 12. Movement of the test probe 32 within the hollow interior of the inner tubular member 12 may be accomplished either manually or through the use of an appropriate linear drive device in a conventional manner.

The eddy current readings obtained will thus correspond to the eddy current responses which would be expected in a tube having a configuration corresponding to the configuration of the annular chamber 16 and having a discontinuity in the wall thereof which corresponds to the configuration and position of the simulator portion 62. In this regard, in accordance with the preferred embodiment, a balance coil 84 is stationarily provided within a reference tube 86 corresponding in size to the size of the annular chamber 16 and having an electrical conductivity corresponding to the conductivity of the liquid mercury in order than the measurements obtained with the eddy current inspection instrument will be difference measurements, similar to the measurements obtained in conventional inspections of steam generator tubing using eddy current techniques. Such difference measurements are advantageous in connection with eddy current inspection techniques as they provide more sensitive readings. Of course, it is not necessary that difference measurements be utilized. Also, while in the preferred embodiment a balance or reference coil 84 is provided within an actual tube 86 of the desired configuration, difference measurements could also be obtained with an eddy current test probe comprised of two axially space coils which are moved as a unit.

Preferably, the above technique will be repeated to obtain eddy current responses at different frequencies of oscillating current applied to the test probe 32, as is conventional. In this regard, in some instances it may be desirable to use a different type of test probe for different frequencies. Changing of the test probe 32 can be easily accomplished with the present invention without the necessity of disassembling the apparatus 10. More particularly, all that is necessary is to withdraw the test probe 32 through one of the end plates 18, 20 and insert a different test probe which may be more sensitive for a different frequency.

Once a set of eddy current responses have been obtained with respect to a particular position of the defect simulator member 48, the knurled wheel 74 may be rotated again to reposition the defect simulator member 48 at a different location within the mercury tube, and a further set of readings obtained. By repeating this operation a number of times, a family of curves can be generated for different radial positions or depths of a particular type of discontinuity.

As noted hereinabove, with the present invention it is possible to simulate virtually any type of discontinuity which might be expected in a tube. In this regard, it is a relatively simple matter to change defect simulator members 48 so that eddy current tests can be conducted thereon to obtain calibration data for different types of discontinuities. In most instances, all that is necessary to simulate different types of discontinuities to withdraw the defect simulator member 48 from the insert member 44 and substitute therefor a defect simulator member having a different simulator portion 62 thereon corresponding to the type of discontinuity on which eddy current tests are to be conducted. In the preferred embodiment, the simulator portion or section 64 of the defect simulator member 48 is removably attached to the seal section 64, such as by means of a friction fit in a bore provided in the lower end of the seal section 64. Therefore, after the defect simulator member 48 is removed from the insert member 44, the simulator portion 62 thereof can be removed and a new simulator portion attached to the seal section 64. The defect simulator member 48 with the new simulator portion 62 may then be reinserted into the insert member 44 and new eddy current tests conducted with respect thereto. Alternatively, the simulator portion 62 and seal section 64 could be integrally formed and removably joined to the anti-rotation section to permit easy exchanging of the simulator portions 62. Still further, separate integrally formed defect simulator members 48 could be provided, each having a different simulator portion or section 62. In the latter case, the seal sections 64 of the different defect simulator members 48 would be identical so that the lower bore 46a in the insert member 44 will be sealed when the different defect simulator members 48 are supported in the insert member 44. In some instances, for larger or very differently configured simulator portions 62 in which a different size sealing section 64 is used, it may be necessary to remove the insert member 44 from the support block 50 as well and substitute a different insert member 44 having a bore therein which corresponds to the size and configuration of the sealing section 64 of the new defect simulator member 48.

Here it is important to note that in order to accomplish changing of the apparatus 10 to effect different types of simulations, it is not necessary to disassemble the entire apparatus 10, and in particular the inner and outer tubes 12, 14 and concentric support arrangement thereof. Rather, all that is necessary is to change the defect simulator member 48 and, in some instances, the insert member 44. During such changing operations, the mercury in the annular chamber 16 may remain there in place and does not have to be drained. In practice, however, it may be desirable to drain a small portion of the mercury so that spillage thereof does not occur during insertion of a new defect simulator member 48 and/or insert member 44.

Typical examples of simulator portions 62 which may be utilized with the apparatus 10 of the present invention are shown in FIGS. 3-6. More particularly, in FIG. 3, the simulator portion 62 comprises a small cylinder made of a nonelectrically conductive material, such as plastic, which is designed to simulate a flat bottom hole in a tube. By movement of the small cylinder to various radial positions through the tube wall, the small plastic cylinder will displace a corresponding volume of mercury and therefore produce eddy current responses representative of a small cylindrical hole in the wall of a tube. FIG. 4 illustrates the configuration of a simulator portion 62a which would be used for simulating round bottom holes, the simulator portion 62a comprising a small cylinder made of plastic material and having a rounded bottom. FIG. 5 illustrates the type of simulator portion 62b which would be used for simulating small spherical voids. In the FIG. 5 embodiment, the simulator portion 62b comprises a metallic rod 88 having a plastic ball 90 positioned therein which will thus simulate a spherical void area in a tube wall. Here it should be noted that the metallic rod portion 88 of the simulator portion 62c shown in FIG. 5 should have an electrical conductivity which corresponds to the electrical conductivity of the mercury in the annular chamber 16 so that the metallic rod portion 88 will not function as a void or flaw when eddy current tests are conducted. It is also possible with the present invention to simulate cracks in a tube wall by providing a simulator portion 62c comprised of a thin rectangular plate. If holes 92 are provided through the plate, such as shown in FIG. 6, the simulation produced would correspond to intermittent bridging of the crack in the wall of the tube, i.e., portions of the wall of the tube would extend across the crack. Also by providing more holes 92, a tighter crack could be simulated. Without holes, the simulator portion 62c would simulate notches or an open crack in the wall of a tubular member.

Of course, it will be appreciated that many other types of discontinuities could be simulated with other simulator portions 62. For example, an inclusion in which a material different from the base metal is trapped in a tubular wall could be simulated by providing a simulator portion 62 made of an electrically conductive material having an electrical conductivity different from that of mercury or of the reference liquid material provided between the inner and outer tubular members 12, 14. Also, with the present invention it is quite easy to simulate discontinuities of odd shapes by constructing the simulator portion 62 of the desired shape.

The use of liquid mercury as the material provided between the inner and outer tubes 12, 14 is particularly desirable in accordance with the present invention as the electrical conductivity of mercury substantially corresponds to the electrical conductivity of the material of which steam generator tubing is made. However, even if the electrical conductivity were different, or if a different type of material were used, the eddy current readings obtained with the apparatus 10 of the present invention would only have to be scaled in accordance with well-known mathematical relationships relating electrical conductivity to the types of eddy current responses obtained.

Further as noted above, the configuration of the inner and outer tubes 12, 14 is such that the annular chamber 16 corresponds to the configuration of the actual tubes on which calibration data is desired. Also, the test probe 32 similarly corresponds to the configuration of the probes used in connection with performing actual measurements and inspections on actual tubing. However, it should be noted that the size of the annular chamber 16 having the mercury therein and the test probe 32 need not be precisely identical to that of an actual steam generator tube and the test probes used to conduct measurement thereon, but instead they may be geometrically scaled so that the calibrations obtained will be representative of the types of readings which would be expected in connection with actual steam generator tubing inspections. In this regard, such geometric scaling of the dimensions of the tubes and the test probe is presently done in connection with the construction of actual physical samples having machined discontinuities therein. Thus, and as noted above, the techniques presently used in connection with actual physical samples having machined discontinuities therein for generating calibration data with respect to the particular types of discontinuities are the same types of techniques which would be used in connection with the present invention which simulates, with greater ease and in a less time consuming manner, such machined discontinuities.

Here it should be noted that all of the various components of the simulator apparatus 10, with the exception of the liquid mercury and the eddy current test probe 32, and in some instances portions of the defect simulator member 48, are made of a nonelectrically conductive material so that eddy currents will only be set up within the mercury itself. In this regard, when a nonelectrically conductive material is utilized, no eddy currents will be induced therein as the magnetic field of the coil or probe 32 is moved therepast. In terms of the defect simulator member 48, in order to simulate different types of discontinuities, which are normally considered to comprise cracks, holes or void areas within a tube, the defect simulator member 48 will necessarily be constructed, at least partially, of a nonelectrically conductive material. As noted above, in some instances, such as with respect to the simulator portion 46b shown in FIG. 5 and when inclusions are being tested, the simulator portion 62 may be constructed of an electrically conductive material or at least partially of electrically conductive material.

Because of the ease with which different types of discontinuities can be simulated, the apparatus of the present invention is particularly useful in connection with establishing better correlations between eddy current responses and the nature and extent of degradations in actual tubing. For example, with the present invention, phase angle measurements and amplitude measurements as a function of test frequency can be easily made for different types of discontinuities which may lead to the development of new calibration standards which will be better able to distinguish between different types and sizes of discontinuities. Furthermore, since a great variety of discontinuities can be simulated, and therefore eddy current test data or responses obtained with respect to each such type of discontinuity for each position, even if new calibration standards are not developed, the additional data capable of being obtained with the present invention may lead to improved understanding of eddy current inspection concepts and the responses obtained.

Thus, it will be appreciated that in accordance with the present invention, calibration data for eddy current inspection testing of tubes can be quite easily obtained with a minimum amount of effort and expense. In particular, virtually any type of discontinuity within a tube can be simulated with the apparatus 10 of the present invention, with different types of discontinuities being simulated without the necessity of having to completely disassemble the apparatus 10, and in particular disassemble and remove the mercury from between the inner and outer tubes 12, 14. Briefly, all that is necessary is to simply remove the defect simulator member 48 and replace it with a defect simulator member having a different simulator portion 62 corresponding to a different type of defect. Furthermore, by virtue of the apparatus 10 of the present invention, adjustment of the depth or position of the simulated discontinuities within the apparatus 10 can be easily and quickly accomplished. Also, with the apparatus 10 of the present invention, changing of test probes or coils 32, more suitable for different frequencies, can be easily accomplished without the necessity of having to disassemble the apparatus.

Therefore, it will be appreciated that the apparatus in accordance with the present invention offers great advantages in terms of improved flexibility and capability for obtaining eddy current calibration data with respect to tubular members in a relatively simple, inexpensive and noncomplex manner. This is accomplished in accordance with the present invention with a simulation apparatus 10 comprised of inner and outer tubular members 12, 14 arranged to define an annular chamber 16 having a predetermined tubular configuration, the outer tubular member 12 having an opening 42 through the wall thereof and the inner tubular member 12 having an axial extending hollow interior extending along the axis thereof. A supply of electrically conductive material is provided in the annular chamber 16, the quantity of liquid material being such as to substantially completely fill the annular chamber 16 in the vicinity of the opening 42 of the wall of the other tubular member. A defect simulator member 48 is supported in the opening 42 in the outer tubular member 14 for movement along a predetermined direction extending transversely of the axis of the inner tubular member 12, the defect simulator member 48 including a simulator portion 62 adapted to be placed in the electrically conductive liquid material in the annular chamber 16. The simulator portion 62 has a predetermined configuration corresponding to the predetermined type of discontinuity in a tube and is made at least partially of a material having an electrical conductivity which is different from that of the liquid material. Adjustment means 74 are provided for adjusting the position of the simulator portion 62 within the annular chamber 16 along the predetermined direction. Also, the apparatus 10 includes an eddy current test probe 32 positioned in the hollow interior of the inner tubular member 12 adjacent to the position of the defect simulation member 48 for generating eddy current responses which are representative of the eddy current responses which would be obtained for a tube having a configuration corresponding to the predetermined tubular configuration and having a discontinuity in the wall thereof corresponding to the predetermined type of discontinuity.

While the preferred embodiments of the present invention has been shown and described, it will be understood that such are merely illustrative and that changes may be made without departing from the scope of the invention as claimed.

What is claimed is:

1. A simulation apparatus for simulating and analyzing discontinuities in a tube using eddy current inspection techniques, said simulation apparatus comprising:
   an inner tubular member and an outer tubular member arranged to define an annular chamber having a predetermined tubular configuration, said outer tubular member having a wall and an opening through the wall, and said inner tubular member including an axially extending hollow interior extending along the axis of said inner tubular member;
   a supply of electrically conductive liquid material in said annular chamber, the quantity of said liquid material being such as to substantially completely fill said annular chamber in the vicinity of said opening through the wall of said outer tubular member;
   a defect simulation member supported in said opening in said outer tubular member for movement along a predetermined direction extending transverse to said axis of said inner tubular member, said defect simulator member including a simulator portion placed in said electrically conductive liquid material in said annular chamber, said simulator portion having a predetermined configuration corresponding to a predetermined type of discontinuity in a tube and being made at least partially of a material having an electrical conductivity different from the electrical conductivity of said liquid material;
   adjustment means for adjusting the position of said simulator portion within said annular chamber along said predetermined direction; and
   an eddy current test probe positioned in said hollow interior of said inner tubular member adjacent to the position of said defect simulation member for generating eddy current responses which are representative of eddy current responses for a tube having a configuration corresponding to said predetermined tubular configuration and having a discontinuity in the wall thereof corresponding to said predetermined type of discontinuity.

2. The simulation apparatus of claim 1, further including end support means for supporting the ends of said inner tubular member and said outer tubular member in concentric relationship, said end support means including means defining a probe opening communicating with said hollow interior of said inner tubular member through which said eddy current test probe is insertable into said hollow interior.

3. The simulation apparatus of claim 2 wherein said end support means comprises a pair of end support plates for supporting the ends of said inner tubular member and said outer tubular member, each of said end plates including a pair of annular concentric grooves therein for receiving the ends of said inner and outer tubular members, and means for securing said end plates to said outer tubular member to thereby secure said inner tubular member in concentric relationship with respect to said outer tubular member.

4. The simulation apparatus of claim 3 wherein said means for securing said end plates to said outer tubular member comprises a pair of stationary support members secured to said outer tubular member adjacent the ends thereof and means for attaching said end plates to said stationary support members.

5. The simulation apparatus of claim 3, further including means for filling said annular chamber with said supply of electrically conductive liquid material.

6. The simulation apparatus of claim 5 wherein said means for filling comprises an aperture through one of said end plates in communication with said annular chamber defined between said inner and outer tubular members.

7. The simulation apparatus of claim 6, further including vent means for venting air in said annular chamber, said vent means comprising a vent hole in one of said end plates in communication with said annular chamber.

8. The simulation apparatus of claim 3 wherein said probe opening for insertion of said eddy current test probe is provided in at least one of said end plates and is in alignment with said hollow interior of said inner tubular member, said probe opening being of a configuration corresponding to the cross sectional configuration of said hollow interior.

9. The simulation apparatus of claim 1, further including a removable insert member removably supported in said opening in sealing relationship therewith, said removable insert member including a surface conforming to the inner surface of said outer tubular member when said insert member is supported in said opening and having a bore therethrough extending in said predetermined direction for receiving said defect simulation member for movement along the axis of said bore, and wherein said adjustment means is operative to adjust the position of said defect simulation member relative to said removable insert member.

10. The simulation apparatus of claim 9, further including support means for removably supporting said insert member in said opening in said side wall of said outer tubular member.

11. The simulation apparatus of claim 9, wherein said defect simulation member comprises an elongated member having said simulator portion at the end thereof and a seal section of a predetermined cross section, wherein said bore of said removable insert member has a cross sectional configuration corresponding to said predetermined cross section of said seal section for receiving said seal section of said elongated member for sliding movement along the axis of said bore.

12. The simulation apparatus of claim 11, further including means for preventing rotation of said elongated member within said bore.

13. The simulation apparatus of claim 12 wherein said means for preventing rotation comprises a pin mounted in said insert member extending transversely of the axis of said bore and an elongated slot in said elongated member for receipt of said pin, said elongated slot being arranged to extend in a direction parallel to said axis of said bore.

14. The simulation apparatus of claim 11, wherein said adjustment means adjustably supports said elongated member for movement relative to said insert member.

15. The simulation apparatus of claim 14, wherein said adjustment means comprises a wheel member threadably connected to a portion of said defect simulation member, and wherein said insert member includes a stop member for engagement by said wheel member whereby rotation of said wheel member serves to move said elongated member along said axis of said bore.

16. The simulation apparatus of claim 1, further including indicator means coupled to said defect simulation member for indicating the position of said simulator portion within said annular chamber.

17. The simulation apparatus of claim 1 wherein said eddy current test probe is mounted for sliding movement within said hollow interior or said inner tubular member past said defect simulator member.

18. The simulation apparatus of claim 1, further including a reference tube and a reference test probe therein for generating with said eddy current test probe differential eddy current responses.

19. The simulation apparatus of claim 1 wherein said simulator portion comprises a cylinder of a predetermined diameter and having a flat bottom end.

20. The simulation apparatus of claim 1 wherein said simulator portion comprises a cylinder of a predetermined diameter and having a rounded end.

21. The simulation apparatus of claim 1 wherein said simulator portion comprises a plate having predetermined dimensions.

22. The simulation apparatus of claim 21 wherein said plate has holes extending therethrough.

23. The simulation apparatus of claim 1 wherein said simulator portion is at least partially constructed of a nonelectrically conductive material.

24. The simulation apparatus of claim 1 wherein said simulator portion is constructed at least partially of a metallic material.

25. The simulation apparatus of claim 24 wherein said metallic material has an electrical conductivity corresponding to the electrical conductivity of said liquid material.

26. The simulation apparatus of claim 7 wherein said liquid material comprises mercury.

* * * * *